US011686611B2

(12) United States Patent
Gulbahar et al.

(10) Patent No.: US 11,686,611 B2
(45) Date of Patent: Jun. 27, 2023

(54) ACOUSTO-OPTIC TRANSDUCER, ARRAY AND METHOD

(71) Applicants: VESTEL ELEKTRONIK SANAYI VE TICARET A.S., Manisa (TR); OZYEGIN UNIVERSITESI, Istanbul (TR)

(72) Inventors: Burhan Gulbahar, Manisa (TR); Gorkem Memisoglu, Manisa (TR)

(73) Assignees: VESTEL ELEKTRONIK SANAYI VE TICARET A.S., Manisa (TR); OZYEGIN UNIVERSITESI, Istanbul (TR)

( * ) Notice: Subject to any disclaimer, the term of this patent is extended or adjusted under 35 U.S.C. 154(b) by 975 days.

(21) Appl. No.: 16/487,361

(22) PCT Filed: Feb. 24, 2017

(86) PCT No.: PCT/EP2017/054408
§ 371 (c)(1),
(2) Date: Aug. 20, 2019

(87) PCT Pub. No.: WO2018/153484
PCT Pub. Date: Aug. 30, 2018

(65) Prior Publication Data
US 2020/0068318 A1    Feb. 27, 2020

(51) Int. Cl.
*G01H 9/00* (2006.01)
*A61B 5/00* (2006.01)
*H04R 23/00* (2006.01)

(52) U.S. Cl.
CPC ............. *G01H 9/00* (2013.01); *A61B 5/0097* (2013.01); *H04R 23/008* (2013.01)

(58) Field of Classification Search
CPC ............................... H04R 23/008; G01H 9/00
See application file for complete search history.

(56) References Cited

U.S. PATENT DOCUMENTS

| 4,166,932 A | 9/1979 | Selway |
| 4,744,625 A | 5/1988 | Lanzisera |

(Continued)

FOREIGN PATENT DOCUMENTS

| CN | 1488232 A | 4/2004 |
| CN | 1977236 A | 6/2007 |

(Continued)

OTHER PUBLICATIONS

Bian et al. "Förster Resonance Energy Transfer Between Molecules in the Vicinity of Graphene-Coated Nanoparticles." Plasmonics (Norwell, Mass.) 11.5 (2016): 1239-1246. Web. (Year: 2016).*
Chinese Office Action & Search Report (with English Machine Translation), dated Apr. 23, 2021, Application No. 201780087311.8, Applicant Vestel Elektronik Sanayi Ve Ticaret A.S., Ozyegin Universitesi, 15 Pages.
Japanese Search Report (with English Machine Translation), dated Sep. 14, 2020, Application No. 2019-545294, 41 Pages.

(Continued)

*Primary Examiner* — David Z Huang
*Assistant Examiner* — Jean F Morello
(74) *Attorney, Agent, or Firm* — Brooks Kushman P.C.

(57) ABSTRACT

An acousto-optic transducer comprises a graphene resonator, a substrate, an entry window and an exit window. The graphene resonator bears at least one donor molecule. The substrate bears at least one acceptor molecule. The graphene resonator is responsive to sound to bring the at least one donor molecule within range of the at least one acceptor molecule for Förster resonance energy transfer from the at least one donor molecule to the at least one acceptor molecule to take place. The entry window is arranged to permit incoming light to fall on the at least one donor molecule. The exit window is arranged to allow light emitted by the at least one acceptor molecule to leave the acousto-optic transducer. Thus, the acousto-optic transducer can function as a passive device using only energy derived from ambient light to convert sound into light.

15 Claims, 6 Drawing Sheets

(56) References Cited

U.S. PATENT DOCUMENTS

| | | |
|---|---|---|
| 6,252,656 B1 | 6/2001 | Wu et al. |
| 8,674,388 B2 | 3/2014 | Shioi et al. |
| 9,042,967 B2 | 5/2015 | Dacosta et al. |
| 9,173,573 B2 | 11/2015 | Weiss et al. |
| 9,269,920 B2 | 2/2016 | Yamazaki et al. |
| 9,995,460 B2 | 6/2018 | Verschuuren et al. |
| 10,053,622 B2 | 8/2018 | Halpert et al. |
| 10,593,895 B2 | 3/2020 | Shitagaki et al. |
| 11,038,135 B2 | 6/2021 | Shitagaki et al. |
| 2004/0062406 A1 | 4/2004 | Sakamoto |
| 2008/0154130 A1 | 6/2008 | Weiss et al. |
| 2015/0175747 A1 | 6/2015 | Liu et al. |

FOREIGN PATENT DOCUMENTS

| | | |
|---|---|---|
| CN | 102099671 A | 6/2011 |
| CN | 103081155 A | 5/2013 |
| CN | 103380509 A | 10/2013 |
| CN | 104650862 A | 5/2015 |
| CN | 105702873 A | 6/2016 |
| CN | 106463587 A | 2/2017 |
| JP | 2008185592 A | 8/2008 |
| JP | 2008531104 A | 8/2008 |
| JP | 2010245797 A | 10/2010 |
| JP | 2010536958 A | 12/2010 |
| WO | 2010/076579 A1 | 7/2010 |
| WO | 2015/180976 A1 | 12/2015 |
| WO | 2016/026863 A1 | 2/2016 |
| WO | 2016/054723 A1 | 4/2016 |
| WO | 2016148860 A1 | 9/2016 |

OTHER PUBLICATIONS

Japanese Decision to Grant a Patent (with English Machine Translation), dated Sep. 23, 2020, Application No. 2019-545294, 5 Pages.

Zhaona Wang et al., "Single-excitation dual-color coherent lasing by tuning resonance energy transfer processes in porous structured nanowires", Nanoscale 2015, vol. 37, No. 7, pp. 15091-15098.

Tairan Zhang, "Synthesis and photoluminescence properties of graphene oxide", Chinese Master's Thesis, 2013, Part 1, 43 Pages.

Tairan Zhang, "Synthesis and photoluminescence properties of graphene oxide", Chinese Master's Thesis, 2013, Part 2, 45 Pages.

Tairan Zhang, "Synthesis and photoluminescence properties of graphene oxide", (English Machine Translation), Chinese Master's Thesis, 2013, Part 1, 57 Pages.

Tairan Zhang, "Synthesis and photoluminescence properties of graphene oxide", (English Machine Translation), Chinese Master's Thesis, 2013, Part 2, 58 Pages.

Burhan Gulbahar et al., "Nanoscale Optical Communications Modulator and Acousto-Optic Transduction with Vibrating Graphene and Resonance Energy Transfer", IEEE International Conference on Communications (ICC) 2017, XP033132910, 7 Pages.

Qin Zhou et al., "Graphene electrostatic microphone and ultrasonic radio", Proceedings National Academy of Sciences PNAS, Jul. 21, 2015, vol. 112, No. 29, XP055408542, pp. 8942-8946.

PCT International Search Report dated Sep. 28, 2017, Application No. PCT/EP2017/054408, Applicant Vestel Elektronik Sanayi Ve Ticret A S, 6 Pages.

PCT Written Opinion of the International Searching Authority dated Sep. 28, 2017, Application No. PCT/EP2017/054408, Applicant Vestfi Elektronik Sanayi Ve Ticret A S, 10 Pages.

* cited by examiner

ACOUSTO-OPTIC TRANSDUCER, ARRAY AND METHOD

CROSS-REFERENCE TO RELATED APPLICATION

This application is the U.S. national phase of PCT Application No. PCT/EP2017/054408 filed on Feb. 24, 2017, the disclosure of which is incorporated in its entirety by reference herein.

TECHNICAL FIELD

The present disclosure relates to an acousto-optic transducer, an array of acousto-optic transducers, a plurality of acousto-optic transducers, and a method.

BACKGROUND

Acousto-optic transduction is the conversion of sound energy into light energy and vice versa. A device for transducing sound into light was invented by Alexander Graham Bell in the nineteenth century, which he called the photophone. The transduction of sound energy into electrical energy is, of course, also commonplace in the prior art, and can be carried out by means of a microphone. For example, Q. Zhou, Jinglin Zhenga, Seita Onishi, M. F. Crommie, and Alex K. Zettl "Graphene electrostatic microphone and ultrasonic radio," *Proceedings of the National Academy of Sciences*, vol. 112, no. 29, pp. 8942-8946, 2015, describes the use of a graphene membrane in a microphone that can be used for wireless communication.

However, such prior art devices generally suffer from the problem that they are not scalable to nanoscale dimensions. In addition, existing photophones generally comprise reflective surfaces which are artificially illuminated and which can be disturbed in response to sound waves impinging on them. They rely on modulation of the intensity of the light reflected by the surface, which limits their practicality. The modulation of polychromatic light is not considered, and hybrid communication architectures are not targeted in these prior art systems.

Förster resonance energy transfer is a mechanism whereby energy is transferred from a first light-sensitive donor molecule to a second light-sensitive acceptor molecule. Such light-sensitive molecules are sometimes known as chromophores. In Förster resonance energy transfer (FRET), the donor molecule is firstly stimulated by incident light into an excited state. When brought sufficiently close to an acceptor molecule, the energy of the excited donor molecule is transferred to the acceptor molecule, which then emits light as a result. The typical range within which the donor molecule must be brought to be sufficiently close to the acceptor molecule for this energy transfer to occur is of the order of about 1 to 10 nanometres. FRET is extremely sensitive to the separation of the donor and acceptor chromophores, since the efficiency of the energy transfer is proportional to the sixth power of the separation between the donor molecule and the acceptor molecule. The intensity of the light emitted by the acceptor molecule may therefore be used as a sensitive measure of the separation between the donor molecule and the acceptor molecule.

SUMMARY

It is therefore an object of the disclosure to provide an acousto-optic transducer, an array of acousto-optic transducers, a plurality of acousto-optic transducers arranged in a two-dimensional grid, and a method of converting sound into light.

The object is solved by an acousto-optic transducer according to the disclosure. The acousto-optic transducer at least comprises a graphene resonator, a substrate, an entry window and an exit window. The graphene resonator bears at least one donor molecule. The substrate bears at least one acceptor molecule. The graphene resonator is responsive to sound to bring the at least one donor molecule within range of the at least one acceptor molecule for Förster resonance energy transfer (FRET) from the at least one donor molecule to the at least one acceptor molecule. The entry window is arranged to permit incoming light to fall on the at least one donor molecule, and the exit window is arranged to allow light emitted by the at least one acceptor molecule to leave the acousto-optic transducer.

This solution is beneficial because it allows the acousto-optic transducer to be manufactured at a nanoscale, to be adjusted in sensitivity to different volumes or amplitudes of sound, for example by varying the separation between the donor molecule and the acceptor molecule, and to be tuned to emit different wavelengths of light by adjusting the constitution of the donor molecule and/or the acceptor molecule in one of several different ways which will be explained in further detail below. Moreover, the donor molecule may be illuminated with ambient light, thereby allowing the acousto-optic transducer to be operated as a passive device, which does not require any electrical power to operate. The acousto-optic transducer may therefore be used for energy harvesting in certain applications, as well as in nanotechnological and biomedical applications, in a way not previously possible with prior art photophones.

Advantageous embodiments of the disclosure may be configured according to any claim and/or part of the following description.

Preferably, at least one of the at least one donor molecule and the at least one acceptor molecule comprises a quantum dot. A quantum dot is a nanoscale particle having quantum properties, which may include their optical and/or electronic properties, which differ from the properties of particles made of similar materials, but at larger scales, as a result of quantum effects. Thus, for example, at least one of the at least one donor molecule and the at least one acceptor molecule may be coated onto a nanoscale particle or otherwise embodied as a quantum dot, and the optical properties of the donor molecule and/or of the acceptor molecule may be varied according to choice, by adjusting one or more properties of the nanoscale particles, such as their size and/or shape.

Preferably, at least one of the at least one donor molecule and the at least one acceptor molecule comprises an inorganic compound of a group 12 element with a group 16 element (in other words, a compound of a group IIB element with a group VIB element under the former IUPAC group nomenclature). Such II-VI compounds have desirable optical properties, which can be engineered to suit different applications.

If so, the inorganic compound is preferably selected from a group consisting of cadmium sulphide, cadmium selenide, zinc sulphide and zinc selenide.

Alternatively or additionally, at least one of the at least one donor molecule and the at least one acceptor molecule preferably comprises an organic compound. This has the advantage of allowing the acousto-optic transducer to be used in biochemical, biomedical, genetic and other bioengineering applications.

If so, the organic compound is preferably selected from a group consisting of a fluorescent protein and a rylene dye.

Preferably, the graphene resonator comprises a graphene membrane. If so, the graphene membrane may be a monolayer or a multi-layer graphene membrane. In other possible embodiments, however, the graphene resonator may have a different physical configuration than a membrane, such as a whisker.

Further preferably, at least one of the entry window and the exit window comprises at least one of a filter and a lens. This is beneficial because it allows the properties of the incoming light incident on the donor molecule and of the might emitted by the acceptor molecule to be adjusted as desired, to suit different applications.

The present disclosure also relates to an array of acousto-optic transducers as described herein, wherein each of the acousto-optic transducers is tuned to emit light of a different wavelength from other acousto-optic transducers of the array. This is beneficial because it allows for the modulation of polychromatic light according to the sound incident on the acousto-optic transducers.

The present disclosure further relates to a plurality of acousto-optic transducers as described herein arranged in a two-dimensional grid. This is beneficial because it can be used to increase the intensity of the light emitted by the acousto-optic transducers of a given wavelength to be increased as desired by increasing the number of acousto-optic transducers in the grid. However, it also allows for digital conversion of sound into light dependent on the location of the acousto-optic transducers in the grid.

In one possible preferred embodiment, the plurality of acousto-optic transducers may comprise a plurality of arrays of transducers, wherein each of the acousto-optic transducers in each array is tuned to emit light of a different wavelength from other acousto-optic transducers of the same array. This is beneficial because it combines the advantages of modulating polychromatic light with the advantages of increasing the intensity of the emitted light and digital resolution of sound volumes or amplitudes.

The present disclosure further relates to a method of converting sound into light. The method at least comprises disposing at least one donor molecule on a graphene resonator, disposing at least one acceptor molecule on a substrate, applying a sound to the graphene resonator of sufficient volume to bring the at least one donor molecule within range of the at least one acceptor molecule for Förster resonance energy transfer (FRET) from the at least one donor molecule to the at least one acceptor molecule, illuminating the at least one donor molecule with light, and emitting light from the at least one acceptor molecule.

Preferably, the method comprises illuminating the at least one donor molecule with ambient light. This is advantageous because the acousto-optic transduction may be carried out by a passive device, not requiring any external electrical power supply and can be used for energy harvesting.

In one possible preferred embodiment, the method comprises altering at least one of the sensitivity and the resonant frequency of the graphene resonator by adjusting at least one of the following: the separation of the graphene resonator from the substrate, a dimension of the graphene resonator, such as its height or its radius, and at least one mechanical property of the graphene resonator, such as its stiffness.

Alternatively or additionally, at least one of the at least one donor molecule and the at least one acceptor molecule respectively comprises a quantum dot, and the method preferably comprises altering a wavelength of the emitted light by changing at least one of the size, the shape, and the chemical composition of at least one of the respective quantum dots.

The present disclosure further relates to a computer program product or a program code or system for executing one or more than one of the herein described methods.

Further features, goals and advantages of the present disclosure will now be described in association with the accompanying drawings, in which exemplary components of the disclosure are illustrated. Components of the devices and methods according to the disclosure which are at least essentially equivalent to each other with respect to their function can be marked by the same reference numerals, wherein such components do not have to be marked or described in all of the drawings.

In the following description, the disclosure is described by way of example only with respect to the accompanying drawings.

DETAILED DESCRIPTION

Figure 1A:
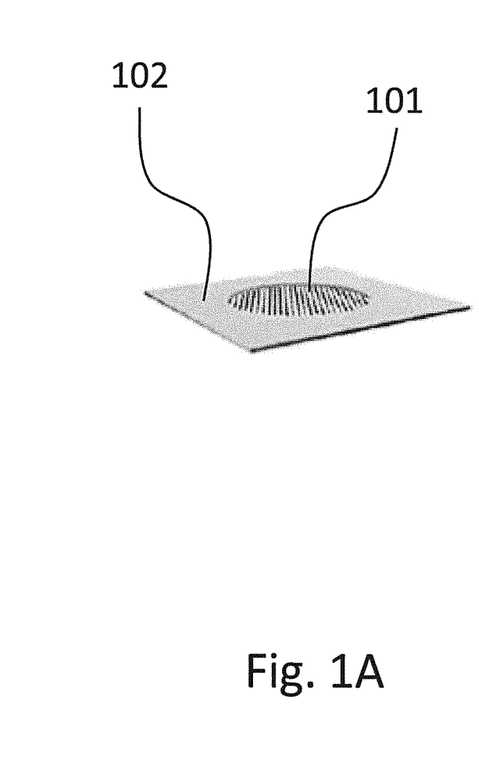
FIGS. 1A, 1B and 1C are a series of schematic diagrams representing successive stages in the construction of an acousto-electric transducer comprising a graphene membrane.
Figure 1B:
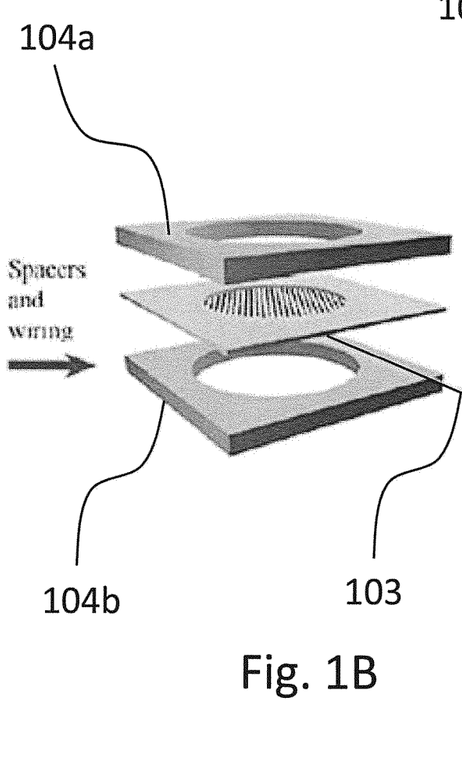
Figure 1C:
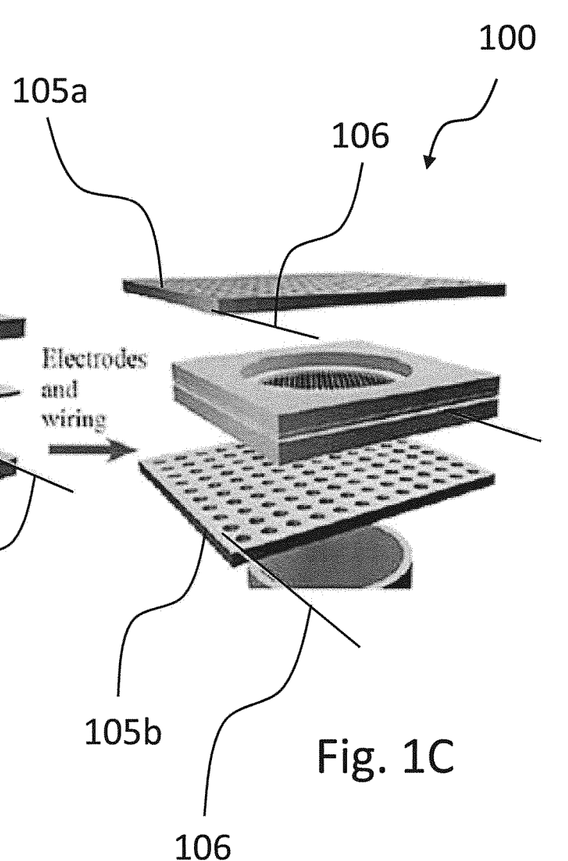

FIGS. 1A, 1B and 10 schematically show successive stages in the construction of an acousto-electric transducer or microphone 100. As shown in FIG. 1A, the acousto-electric transducer 100 comprises a graphene membrane 101, which is suspended across an aperture of a supporting frame 102. As shown in the exploded diagram of FIG. 1B, the graphene membrane 101 is electrically contacted with a gold wire 103 and the supporting frame 102 is mounted between a pair of spacers 104a, 104b. As shown in the exploded diagram of FIG. 10, the resulting subassembly is then sandwiched between a pair of gold-coated stationary electrodes 105a, 105b, to each of which a gold wire 106 is attached to make an electrical contact. When sound waves impinge on the graphene membrane 101, the graphene membrane 101 is caused to mover thereby, and the electrical properties of the graphene membrane 101 relative to the two stationary electrodes 105a, 105b change accordingly. During such operation, the acousto-electric transducer 100 may be modelled as a current source.

Figure 2:
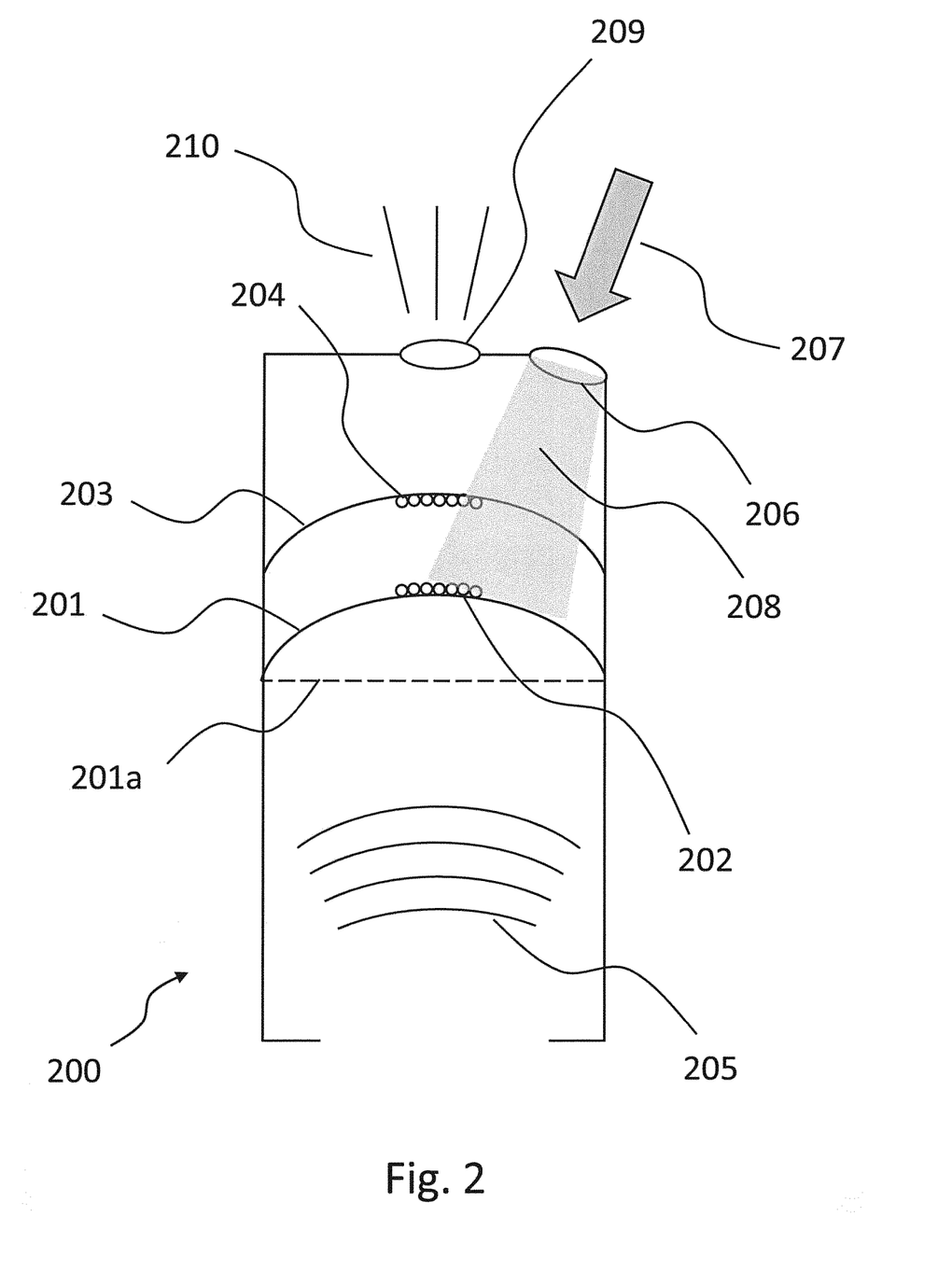
FIG. 2 is a schematic diagram of an embodiment of an acousto-optic transducer.

FIG. 2 shows an embodiment of an acousto-optic transducer 200. The acousto-optic transducer 200 comprises a graphene resonator 201, a substrate 203, an entry window 206 and an exit window 209. The graphene resonator bears a plurality of donor molecules 202 coated on its surface as a thin film. The substrate 203 bears a plurality of acceptor molecules 204 coated on the surface of the substrate 203 as a thin film facing the thin film of donor molecules 202. The graphene resonator 201 is responsive to sound waves 205 and moves during operation of the acousto-optic transducer 200 from a rest position, represented in FIG. 2 by the dashed line 201a, to a displaced position, as shown. This movement of the graphene resonator 201 brings the donor molecules 202 within range of the acceptor molecules 204 close enough for Förster resonance energy transfer (FRET) from the donor molecules 202 to the acceptor molecules 204 to take place. The entry window 206 is arranged to permit incoming ambient light 207 to fall 208 on the donor molecules 202, thereby stimulating them into an excited state. The entry window 206 comprises a bandpass filter, in order to filter out wavelengths of ambient light 207 other than those which are required to excite the donor molecules 202. The exit window 209 is arranged to allow light 210 emitted by the acceptor molecules 204 as a result of the FRET from the donor molecules 202 to the acceptor molecules 204 to leave the acousto-optic transducer 200. The exit window 209 comprises a collimating lens to focus the emitted light 210.

Figure 3A:
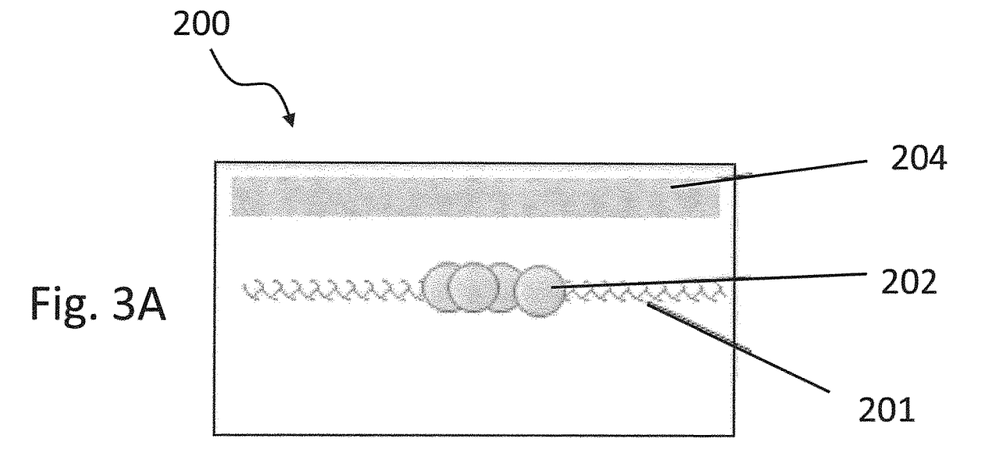
FIGS. 3A, 3B and 3C schematically represent different phases in the movement of a graphene resonator in an acousto-optic transducer.
Figure 3B:
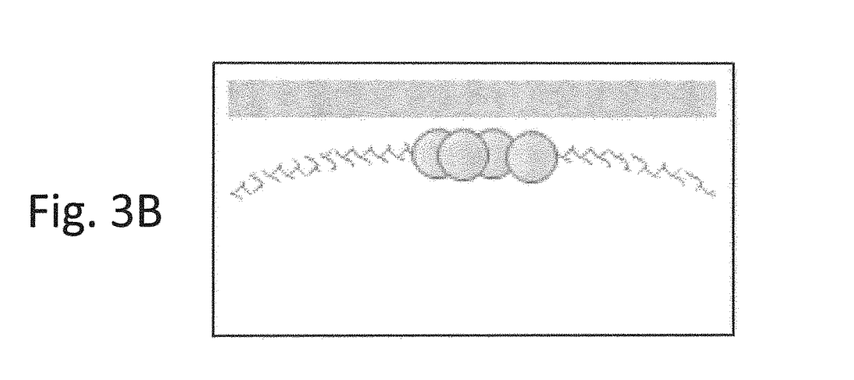
Figure 3C:
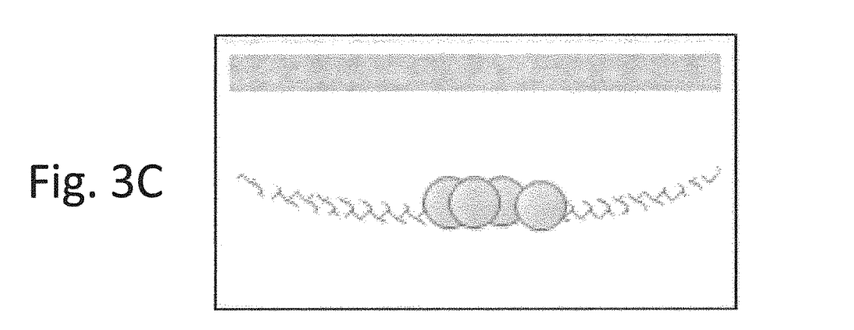

FIGS. 3A, 3B and 3C show different phases in the movement of a graphene resonator 201 in an acousto-optic transducer 200 during its operation. The graphene resonator 201 bears particles of a donor molecule 202, which may, for example, be cadmium selenide or zinc sulphide quantum dots, tuned to be an emitter of blue-green light, coated on to a surface of the graphene resonator 201. The acceptor molecules 204 may, for example, be a rylene dye, such as a thin film of peryline, coated on a substrate. In FIG. 3A, the graphene resonator 201 is initially at rest, and the particles of donor molecule 202 borne by the graphene resonator 201 are too far away from the acceptor molecules 204 for Förster resonance energy transfer from the former to the latter to take place. In FIG. 3B, the graphene resonator 201 is displaced towards the acceptor molecules 204 by a sound wave and the donor molecules 202 absorb ambient light and are thereby stimulated into an excited state. Since the particles of donor molecule 202 are now close enough to the thin film of acceptor molecules 204 for FRET to take place, the donor molecules 202 give up their energy to the acceptor molecules 204, which emit light as a result. In FIG. 3C, the graphene resonator 201 rebounds to its anti-phase position. The donor molecules 202 continue to absorb ambient light and are therefore continue to be stimulated into an excited state. However, since they are now too far away again from the acceptor molecules 204 for FRET from the former to the latter to take place, the acceptor molecules 204 cease to emit light until the graphene resonator 201 returns to its position represented in FIG. 3B once again. The light emitted by the acceptor molecules 204 is therefore subject to amplitude modulation at the resonant frequency of the graphene resonator 201.

Figure 4A:
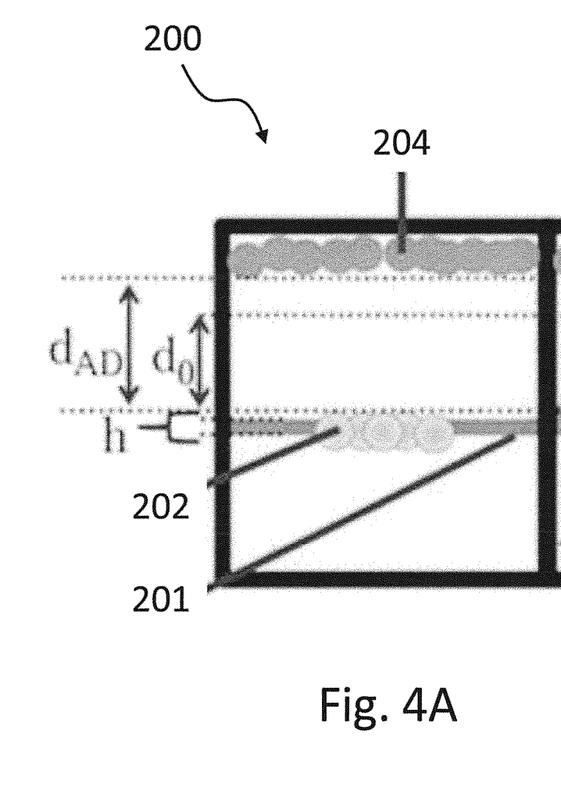
FIGS. 4A, 4B and 4C schematically represent different phases in the operation of an acousto-optic transducer.
Figures 4B, 4C:
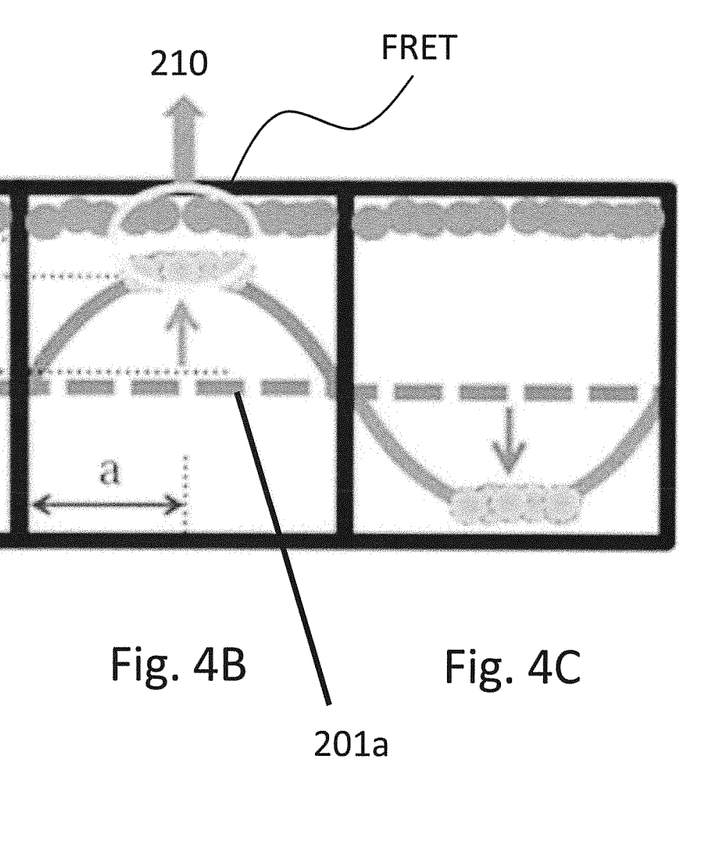

FIGS. 4A, 4B and 4C show different phases in the operation of an acousto-optic transducer 200 during its operation, which respectively correspond to the different phases shown in FIGS. 3A, 3B and 3C. As may be seen in FIG. 4A, when the graphene resonator 201 is in its rest position, the donor molecules 202 are separated from the acceptor molecules 204 by a distance, $d_{AD}$, which is greater than the maximum distance at which FRET from the donor molecules 202 to the acceptor molecules 204 is able to take place. As may be seen in FIG. 4B, when the graphene resonator 201 is displaced by a sound wave, its displacement, $d_0$, is sufficiently large for the donor molecules 202 to be brought within range of the acceptor molecules 204 for FRET from the former to the latter to take place. The graphene resonator 201 has a height, h, and a semi-diameter, a, one or both of which may be varied, in order to change one or both of the resonant frequency of the graphene resonator 201 and its sensitivity to sound waves of different volumes. The separation distance, $d_{AD}$, of the donor molecules 202 from the acceptor molecules 204 may also be varied, in order to alter the resonant frequency or the sensitivity of the graphene resonator 201, as may a mechanical property of the graphene resonator 201, such as its stiffness. This may be altered by adjusting the number of layers of which the graphene resonator 201 is composed, for example.

On the other hand, the wavelength of the light emitted by the acceptor molecules 204 may be altered by changing the chemical composition of either or both of the donor molecules 202 and the acceptor molecules 204. If either or both of the donor molecules 202 and the acceptor molecules 204 are embodied as quantum dots, the wavelength of the light emitted by the acceptor molecules 204 may also be altered by changing the size and/or shape of the quantum dots.

Figure 5:
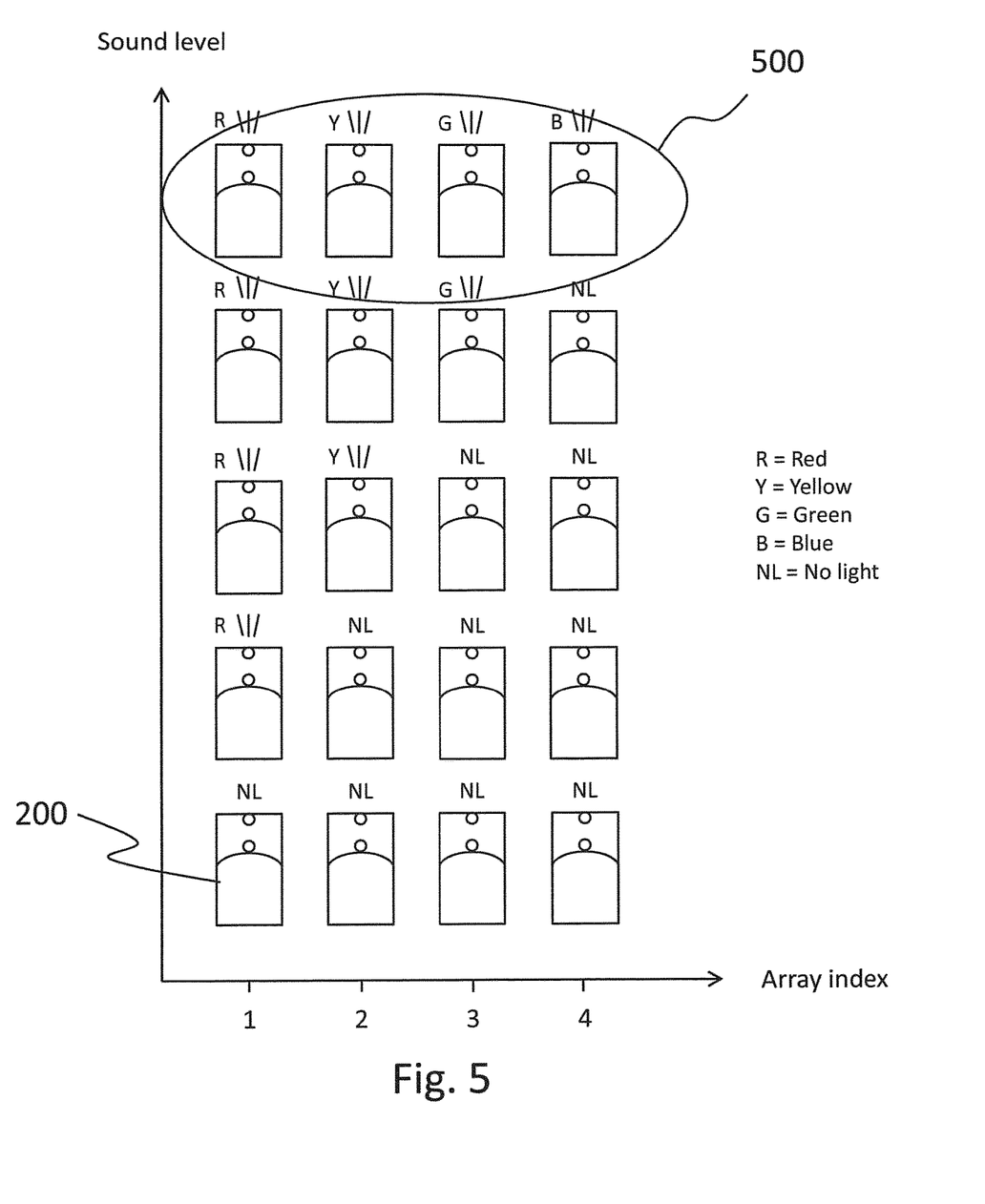
FIG. 5 is a graph schematically representing the different responses of an array of acousto-optic transducers to different sound levels.

FIG. 5 shows an array 500 of acousto-optic transducers and how it responds to different sound levels. The array 500 comprises a plurality of acousto-optic transducers 200 as described above, wherein each of the acousto-optic transducers is tuned to emit light of a different wavelength from other acousto-optic transducers in the array. In the example illustrated in FIG. 5, the array 500 comprises four acousto-optic transducers 200, one of which is tuned to emit red light (labelled "R"), one of which is tuned to emit yellow light (labelled "Y"), one of which is tuned to emit green light (labelled "G") and one of which is tuned to emit blue light (labelled "B"). This example is purely illustrative, however, and such an array of acousto-optic transducers could in other alternative embodiments comprise any different number of acousto-optic transducers, such as 2, 3, 5, 6 and so on, tuned to emit light of any other colours, such as orange, cyan, purple and so on.

In the exemplary embodiment illustrated in FIG. 5, the red-emitting acousto-optic transducer is the most sensitive to low sound levels, the yellow-emitting acousto-optic transducer is the next most sensitive to low sound levels, the green-emitting acousto-optic transducer is less sensitive still, and the blue-emitting acousto-optic transducer is the least sensitive of all the acousto-optic transducers in the array 500. Thus, as the volume or amplitude of the sound impinging on the array 500 is increased, firstly the red-emitting acousto-optic transducer lights up, then the yellow-emitting acousto-optic transducer starts emitting light next, then the green-emitting acousto-optic transducer also starts to emit light as the volume of the incident sound is increased, and finally, the blue-emitting acousto-optic transducer is lit up as the sound volume increases still further. This is illustrated schematically in the graph of FIG. 5 by the five different representations of the same array 500 shown at increasing sound levels.

Figure 6:
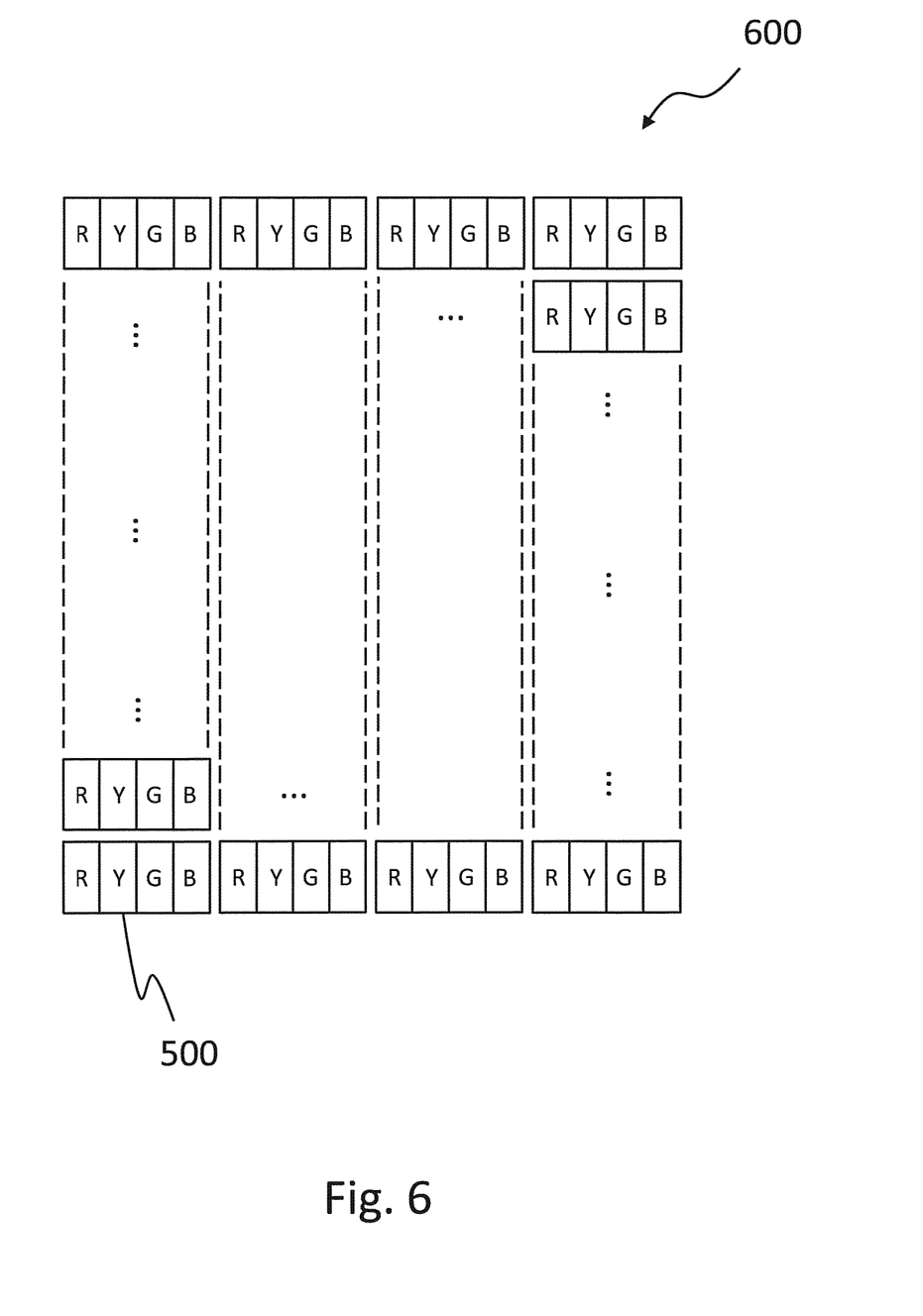
FIG. 6 is a schematic diagram of a plurality of arrays of acousto-optic transducers arranged in a two-dimensional grid.

FIG. 6 show a plurality of such arrays 500 of acousto-optic transducers 200 arranged in a two-dimensional grid 600. In the illustrated embodiment, each of the arrays 500 therefore comprises the same combination of four acousto-optic transducers 200 as each other, one of which emits red light, one of which emits yellow light, one green light, and one blue light. The plurality of arrays 500 are arranged in rows and columns to form the two-dimensional grid 600 in a similar manner to how the pixels of a charge-coupled device (CCD) are arranged, for example. Since each one of the acousto-optic transducers 200 can be manufactured as a microscale or even as a nanoscale device, the entire grid 600 need not be more than a few millimetres in size across each row or column. On the other hand, the acousto-optic transducers 200 can instead be manufactured as macroscale devices, allowing a grid 600 of tens of centimetres or even of metres in each dimension to be constructed. Such two-dimensional grids may, of course, also be combined with each other in a variety of different configurations to make three-dimensional sound-to-light transduction devices as well.

Whereas in the embodiment illustrated in FIG. 6, the arrays 500 are each of the same type as that shown in FIG. 5, this is purely for the sake of example. The arrays could instead comprise different numbers of acousto-optic transducers 200 tuned to different wavelengths and of different sensitivities, so that any possible combination thereof can be achieved. The grid 600 may thus, for example, instead comprise a plurality of acousto-optic transducers 200, all of which are tuned to emit light of the same wavelength as each other, but which are of different sensitivities from each other, so that the intensity of the light emitted in total by the grid varies proportionally to the volume of the sound impinging on the acousto-optic transducers 200 in the grid.

In summary, therefore, the present disclosure provides an acousto-optic transducer 200, which at least comprises a graphene resonator 201, a substrate 203, an entry window 206 and an exit window 209. The graphene resonator 201 bears at least one donor molecule 202 and the substrate 203 bears at least one acceptor molecule 204. The graphene resonator 201 is responsive to sound 205 to bring the at least one donor molecule 202 within range of the at least one acceptor molecule 204 for Förster resonance energy transfer (FRET) from the at least one donor molecule to the at least one acceptor molecule to take place. The entry window 206 is arranged to permit incoming light 207, which is preferably ambient light, to fall on the at least one donor molecule 202. The exit window 209 is arranged to allow light 210 emitted by the at least one acceptor molecule 204 to leave the acousto-optic transducer 200. Thus, the acousto-optic transducer 200 can function as a passive device using only energy derived from ambient light to convert sound into light, and can be tuned to different frequencies and amplitudes of sound by adjusting either or both of the mechanical properties of the resonator 201 and the separation of the resonator from the substrate 203. The frequency of the emitted light can also be varied by changing at least one of the size, the shape, and the chemical composition of particles of the donor or acceptor molecules, for example if they are quantum dots. The acousto-optic transducer can also be realised as a nanoscale device. In other aspects, the present disclosure also provides a method of operating any such acousto-optic transducer, and an array of such acousto-optic transducers, wherein each of the acousto-optic transducers is tuned to emit light of a different wavelength from other acousto-optic transducers in the array.

REFERENCE NUMERALS

| 100 | Acousto-electric transducer |
|---|---|
| 101 | Graphene membrane |
| 102 | Supporting frame |
| 103 | Electrical wiring to graphene membrane |
| 104a, 104b | Spacers |
| 105a, 105b | Electrodes |
| 106 | Electrical wiring to electrodes |
| 200 | Electro-acoustic transducer |
| 201 | Graphene membrane |
| 201a | Rest position of graphene membrane |
| 202 | Donor molecules |

-continued

| 203 | Substrate |
|---|---|
| 204 | Acceptor molecules |
| 205 | Acoustic waves |
| 206 | Entry window |
| 207 | Incoming ambient light |
| 208 | Light falling on donor molecules |
| 209 | Exit window |
| 210 | Emitted light |
| 500 | Polychromatic array of electro-acoustic transducers |
| 600 | Grid of electro-acoustic arrays |

The invention claimed is:

1. An acousto-optic transducer comprising:
at least one donor molecule and at least one acceptor molecule for Förster resonance energy transfer from the at least one donor molecule to the at least one acceptor molecule;
an entry window arranged to permit incoming light to fall on the at least one donor molecule;
an exit window arranged to allow light emitted by the at least one acceptor molecule to leave the acousto-optic transducer;
a graphene resonator bearing the at least one donor molecule; and
a substrate bearing the at least one acceptor molecule;
wherein the graphene resonator is responsive to sound and can be displaced by sound towards the substrate to bring the at least one donor molecule within range of the at least one acceptor molecule for Förster resonance energy transfer from the at least one donor molecule to the at least one acceptor molecule to occur.

2. The acousto-optic transducer according to claim 1, wherein at least one of the at least one donor molecule and the at least one acceptor molecule comprises a quantum dot.

3. The acousto-optic transducer according to claim 1, wherein at least one of the at least one donor molecule and the at least one acceptor molecule comprises an inorganic compound of a group 12 element with a group 16 element.

4. The acousto-optic transducer according to claim 3, wherein the inorganic compound is selected from a group consisting of cadmium sulphide, cadmium selenide, zinc sulphide and zinc selenide.

5. The acousto-optic transducer according to claim 1, wherein at least one of the at least one donor molecule and the at least one acceptor molecule comprises an organic compound.

6. The acousto-optic transducer according to claim 5, wherein the organic compound is selected from a group consisting of a fluorescent protein and a rylene dye.

7. The acousto-optic transducer according to claim 1, wherein the graphene resonator comprises a graphene membrane.

8. The acousto-optic transducer according to claim 1, wherein at least one of the entry window and the exit window comprises at least one of a filter and a lens.

9. An array of acousto-optic transducers according to claim 1, wherein each of the acousto-optic transducers is tuned to emit light of a different wavelength from other acousto-optic transducers of the array.

10. A plurality of acousto-optic transducers according to claim 1 arranged in a two-dimensional grid.

11. A plurality of acousto-optic transducers according to claim 10, comprising a plurality of arrays of transducers.

12. A method of converting sound into light by Förster resonance energy transfer from at least one donor molecule to at least one acceptor molecule, the method comprising:

disposing the at least one donor molecule on a graphene resonator;

disposing the at least one acceptor molecule on a substrate;

illuminating the at least one donor molecule with light;

applying a sound to the graphene resonator to displace the graphene resonator towards the substrate, to bring the at least one donor molecule within range of the at least one acceptor molecule for Förster resonance energy transfer from the at least one donor molecule to the at least one acceptor molecule to occur; and emitting light from the at least one acceptor molecule.

13. The method according to claim 12 wherein illuminating the at least one donor molecule with light comprises illuminating the at least one donor molecule with ambient light.

14. The method according to claim 12 further comprising altering at least one of sensitivity and resonant frequency of the graphene resonator by adjusting at least one of:

separation of the graphene resonator from the substrate;

a dimension of the graphene resonator; or at least one mechanical property of the graphene resonator.

15. The method according to claim 12, wherein at least one of the at least one donor molecule and the at least one acceptor molecule respectively comprises a quantum dot, and the method further comprises altering a wavelength of the emitted light by changing at least one of:

size;

shape; or chemical composition of at least one of the respective quantum dots.

\* \* \* \* \*